United States Patent [19]

Welle et al.

[11] 4,192,893

[45] Mar. 11, 1980

[54] ANTI-DEPRESSIVE COMPOUNDS

[75] Inventors: Hendricus B. A. Welle, Utrecht; Volkert Claassen, Weesp, both of Netherlands

[73] Assignee: U.S. Philips Corporation, New York, N.Y.

[21] Appl. No.: 859,603

[22] Filed: Dec. 12, 1977

Related U.S. Application Data

[63] Continuation of Ser. No. 668,492, Mar. 19, 1976, abandoned.

[30] Foreign Application Priority Data

Mar. 20, 1975 [NL] Netherlands .......................... 7503307

[51] Int. Cl.$^2$ ...................... A61K 31/15; C07C 131/00
[52] U.S. Cl. ..................................... 424/327; 424/316; 260/501.14
[58] Field of Search .................. 260/566 AE, 501.14; 424/316, 327

[56] References Cited

U.S. PATENT DOCUMENTS

| | | | |
|---|---|---|---|
| 3,429,919 | 2/1969 | Koopman et al. | 260/566 AE |
| 3,692,835 | 9/1972 | Van Dijk et al. | 260/566 AE |
| 3,845,126 | 10/1974 | Giraudon et al. | 260/566 AE |

*Primary Examiner*—Gerald A. Schwartz
*Attorney, Agent, or Firm*—Norman N. Spain

[57] ABSTRACT

The novel compounds of formula I and salts thereof have a very powerful anti-depressive activity which for a considerable part, and in some substances even entirely, is based on serotonine potentiation. Moncamino oxidase inhibition does not contribute to the anti-depressive effect. The substances are little toxic and substantially free from side effects.

The compounds can be synthesized and processed to compositions according to known methods.

14 Claims, 12 Drawing Figures

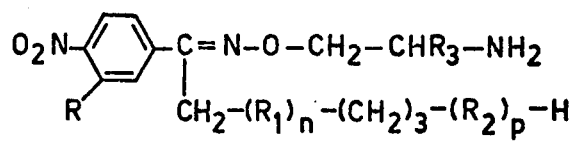 I
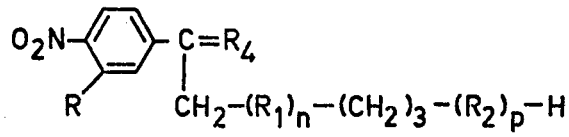 II
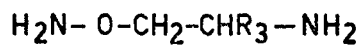 III
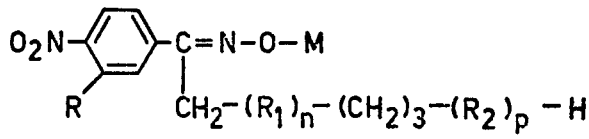 IV
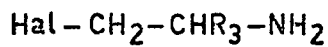 V
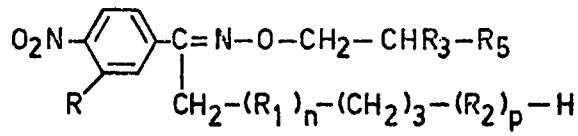 VI
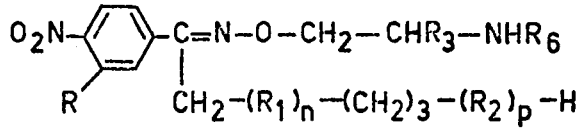 VII
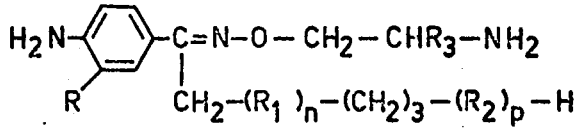 VIII

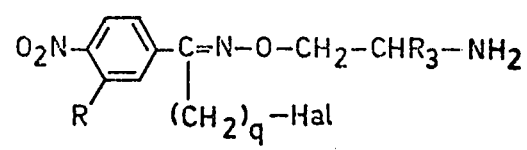
IX
X
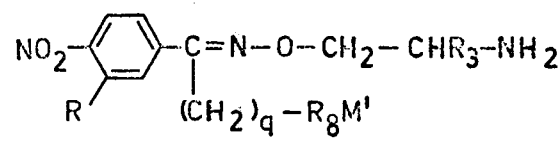
XI
Hal R'₇  XII

ANTI-DEPRESSIVE COMPOUNDS

This is a continuation of application Ser. No. 668,492, filed Mar. 19, 1976, now abandoned.

The invention relates to novel anti-depressive compounds.

British patent specification No. 1,205,665 discloses a large group of oxime ether compounds having anti-depressive activity, which compounds are derived from alkyl-phenyl-ketones. The compounds have attached to a phenyl group one or more substituents which are selected from a very large group. Each of the possible substituents may be bound in any position of the phenyl group, but according to said patent specification substitutions with nitro groups are restricted to the meta-positions.

This suggests that oxime ether compounds which are derived from alkylphenones and which have a nitro-group in a position other than a meta-position, have no anti-depressive activity. The anti-depressive activity of the known compounds is based on monoamino oxidase (MAO) inhibition and/or noradrenaline potentiation.

However, compounds which exhibit monoamino oxidase are particularly difficult to administer. They often have serious side effects and are often incompatible with other medicines and with some nutrients.

Since the regulations governing the use of medicines have become more stringent, only those compounds which are substantially free from side effects can be considered for administration to human beings.

It is the object of the invention to provide compounds having a powerful anti-depressive activity which is expressed inter alia in an elevation of mood of the treated patient but which have no component based on MAO inhibition. The compounds in view should be substantially free from side effects.

It has surprisingly been found that the compounds of formula I of the formula sheet and their salts formed with pharmaceutically acceptable acids satisfy these requirements. In formula I the symbols have the following meanings: R is hydrogen, methyl or chlorine, $R_1$ is oxygen or sulphur, $R_2$ is $OCH_2$, $CH_2OCH_2$, $OC_2H_4OCH_2$, $R_3$ is hydrogen or methyl, n and p are 0 or b 1 and n+p is 0 or 1.

It has surprisingly been found that the anti-depressive activity of these compounds is based for a considerable part, and in some compounds even exclusively, on serotonine potentiation, an activity which in a depressive patient results in an elevation of mood. However, most compounds show, in addition to serotonine potentiation, a very powerful noradrenaline potentiation as an anti-depressive activity component.

The absence of an activity based on MAO inhibition is surprising especially as the compounds proved to be substantially free from side effects, for example, stomach ulceration and bronche constriction, and have a low toxicity.

In the following table properties of the compounds according to the invention are compared with those of the closest related known compounds from British patent specification No. 1,205,665.

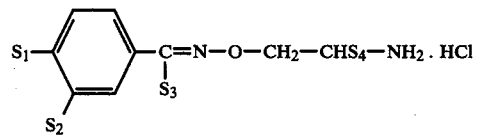

| | Compound | | | noradr. | scrot. | MAO | stomach | broncho- |
|---|---|---|---|---|---|---|---|---|
| | $S_1$ | $S_2$ | $S_3$ | $S_4$ | pot. | pot. | inhib. | ulcer. | constr. |
| 1 | $NO_2$ | H | $(CH_2)_3CH_3$ | H | 6.9 | 3.8 | >215 | — | — |
| 2 | $NO_2$ | H | $CH_2S(CH_2)_2CH_3$ | H | 6.0 | 11 | >215 | — | — |
| 3 | $NO_2$ | H | $CH_2O(CH_2)_2CH_3$ | H | 4.1 | 7.9 | >215 | — | — |
| 4 | $NO_2$ | H | $(CH_2)_4OCH_3$ | H | 11 | 16 | >215 | — | — |
| 5 | $NO_2$ | H | $(CH_2)_4O(CH_2)_2OCH_3$ | H | 3.7 | 16 | >215 | — | — |
| 6 | $NO_2$ | H | $(CH_2)_5OCH_3$ | H | 9.1 | 22 | >215 | — | — |
| 7 | $NO_2$ | $CH_3$ | $(CH_2)_3CH_3$ | H | 5.2 | 8.9 | >215 | — | — |
| 8 | $NO_2$ | Cl | $(CH_2)_4OCH_3$ | H | 6.2 | 14 | >215 | — | — |
| 9 | $NO_2$ | H | $(CH_2)_3CH_3$ | $CH_3$ | >215 | 9.8 | >215 | — | — |
| 10 | $NO_2$ | H | $CH_2O(CH_2)_2CH_3$ | $CH_3$* | >100 | 17 | >215 | — | — |
| 11 | $NO_2$ | Cl | $(CH_2)_4OCH_3$ | $CH_3$* | 31 | 16 | >215 | — | — |
| B1 | H | $NO_2$ | $C_2H_5$ | H | 5.0 | 3.5 | 13 | | |
| B2 | $OCH_3$ | $NO_2$ | $C_2H_5$ | H | 5.8 | 1.7 | 8.8 | | |
| B3 | H | $NO_2$ | $(CH_2)_4CH_3$ | H | 38 | 85 | >215 | + | |

*fumarate 1:1

The numbers in this table are $ED_{50}$ values expressed in mg/kg.

It is remarkable that the compounds 9 and 10 neither potentiate noradrenaline nor inhibit MAO. The anti-depressive activity of these compounds is based entirely on serotonine potentiation.

These compounds therefore and in particular, compound 9 are to be preferred if a very specific serotonine potentiation is desired.

Noradrenaline potentiation and serotonine potentiation in compounds 7 and 8 are of the same order of magnitude. Moreover, the activity is at a high level.

Both noradrenaline potentiation and serotonine potentiation in compound 5 are at a high level but the noradrenaline potentiation is stronger by well over a factor 4.

It appears from the table that the compounds according to the invention are substantially free from undesired side effects.

Although the known compounds B1 and B2 have a strong noradrenaline and serotonine potentiating effect, they also have a powerful MAO inhibition. In compound B3 not only both the noradrenaline potentiation and the serotonine potentiation is of quite a different level, in addition the compound gives stomach ulceration. Therefore, none of the known compounds satisfy the object of the invention.

The data recorded in the table were determined by means of the following tests.

The noradrenaline potentiation was determined in the tetrabenazine test. In this test a quantity of the compound to be tested was administered orally to five male albino mice. After 45 minutes the animals were injected subcutaneously with 80 mg/kg of tetrabenazine. After another 45 minutes the ptosis was determined and compared with the ptosis of animals which had received tetrabenazine alone. The $ED_{50}$ was determined from the results.

The serotonin potentiation was determined in the 5-hydroxytryptophan test. For this purpose the compounds to be tested were administered orally in a series of dosages to isolated male albino mice (5 mice per dosage) 1 hour prior to intraperitoneal administration of 150 mg/kg of dl-5-hydroxytryptophan. 30 minutes after this threshold dosage the mice were observed individually and the following parameters were evaluated: stereotypical shaking of the head, spreading of the hindlegs, tremor, tendency to flee, lordosis and clonic stamping with the frontlegs. The $ED_{50}$ value was calculated from the results.

The monoamino oxydase (MAO) inhibiting effect was determined in experiments in which a quantity of the compound to be tested was administered orally to five male albino mice. One hour later the animals were injected subcutaneously with tryptamine hydrochloride in a quantity of 250 mg/kg. This quantity does not cause mortality in animals which did not receive the compound to be tested, but did cause mortality in animals to which an active substance had been administered. Eighteen hours after the administration of tryptamine hydrochloride it was determined how many treated animals had died. The $ED_{50}$ was determined from the results.

By means of the method by Metyšová, Arzneimittelforschung 13 1039 (1963) it was determined whether the oral administration of 200 mg of a compound to be tested causes stomach ulceration.

By means of the method by Konzett-Rossler, Arch. Esp. Path. Pharmakol, 195 71 (1940) it was investigated whether a compound to be tested causes bronchoconstriction after intravenous administration of 3 mg/kg. Reduction of the breathing function as a result of bronchoconstriction is expressed in this method in a smaller volume of air taken in.

On the basis of their properties the compounds of formula I and their salts are particularly suitable for use in the treatment of depressive patients. This applies in particular to the compounds: 5-(2-methoxyethoxy)-4'-nitrovalerophenone O-(2-aminoethyl)oxime, 4'-nitro-3'-methyl-valerophenone O-(2-aminoethyl)oxime, 3'-chloro-5-methoxy-4'-nitrovalerophenone O-(2-aminoethyl)oxime, 4'-nitrovalerophenone O-(2-aminopropyl)oxime and 3'-chloro-4'-nitro-5-methoxyvalerophenone O-(2-aminopropyl) oxime and their salts.

The quantity, the frequency, and the way in which the compounds according to the invention are administered may differ for each individual patient and also in accordance with the severity of the disturbance to be treated. In general, an oral daily quantity of 25–500 mg will be chosen, as a rule 50–200 mg.

The compounds are preferably used in the form of tablets, coated tablets, capsules, pills, powders, injection liquids and the like. They can be processed to such compositions according to methods which are known per se.

The invention also relates to compositions having a compound of formula I or a salt thereof formed with a pharmaceutically acceptable acid as an active constituent, and to methods to bring the compounds and their salts in a form suitable for administration, for example, by mixing an active substance with or dissolving it in solid or liquid pharmaceutical carrier materials.

As examples of pharmaceutically acceptable acids with which the bases of formula I can form salts may be mentioned: inorganic acids, for example hydrochloric acid, nitric acid, sulphuric acid and organic acids, for example, malic acid, citric acid, fumaric acid, maleic acid, tartaric acid, benzoic acid and the like.

The compounds of formula I and their salts can be prepared according to methods which are known for the preparation of this type of compounds and according to methods analogous thereto.

The invention also relates to the preparation of the compounds.

The compounds can be prepared inter alia by reacting a compound of formula II with a compound of formula III or a salt thereof. In this case $R_4$ is an oxygen atom, an oxime group or an alkylene dioxygroup, for example ethylenedioxy.

The reaction is preferably carried out in an inert solvent, for example an alcohol, dioxan, dimethyl formamide, tetrahydrofuran or a mixture thereof, at temperatures between room temperature and the boiling point of the mixture and possibly in the presence of an acid binder, for example pyridine.

The compounds are also prepared by reacting a compound of formula IV wherein M is a hydrogen atom or an alkali metal atom with a compound of formula V or a salt thereof wherein Hal is a halogen atom, preferably a chlorine atom or a bromine atom.

The reaction is preferably carried out in an inert solvent, for example alcohols, ethers or dimethyl formamide. When M is a hydrogen atom, an acid binder for example an alcoholate is preferably added as well. As a rule the reaction temperature is between 0° and 50° C.

The compounds can also be prepared by reacting a compound of formula VI wherein R5 is a leaving group, for example a mesyloxy group or a tosyloxy group, with ammonia. The reaction is preferably carried out in an inert solvent, for example an alcohol, as a rule at temperatures between room temperature and 150° C.

The compounds of formula VI are prepared by reacting a compound of formula IV in ethanol and in the presence of an alcoholate at temperatures up to 60° C. with ethylene oxide or propylene oxide. The reaction product is then reacting with mesylchloride or tosylchloride dissolved in methylene chloride.

The compounds can also be obtained by removing or protective group $R_6$ by means of hydrolysis from a compound of formula VII. As a protective group may be mentioned, for example, the trityl group. The reaction is carried out, for example, in a water-miscible solvent in acid conditions at a temperature between room temperature and 100° C.

The compounds can also be obtained by converting the para amino(aromatic) group in a compound of formula VIII into a nitro group.

The conversion can be carried out by a reaction with nitrous acid at −10° to +50° C., followed by decomposition of the resulting diazonium compound in the reaction mixture at 20°–75° C. in the presence of copper. The conversion of compounds wherein $R_1$ does not represent sulphur may also be carried out with a peroxide, for example hydrogen peroxide or m-chloroperbenzoic acid, in an inert solvent, for example methylene chloride or chloroform, at temperatures between room temperature and the boiling point of the mixture.

Compounds of formula I wherein $n+p=1$ can furthermore be prepared by reacting a compound of formula IX with a compound of formula X. In these formulae q has the value 1, 4 or 5, M' is an alkali metal atom and $R_7$ is a propoxy group, a propylthio group, a methoxy group or a methoxyethoxy group. Hal is a halogen atom, preferably a chlorine atom or a bromine atom. The reaction may be carried out, for example, in aqueous alcohol at temperatures of 0° C. or possibly lower, to room temperature.

Compounds of formula I wherein $n+p=1$ can also be obtained by reacting a compound of formula XI with a compound of formula XIII. In these formulae q has the value 1, 4 or 5, $R_8$ is an oxygen atom or a sulphur atom, M' is an alkali metal atom, $R'_7$ is a methyl group, a propyl group or a methoxy ethyl group, and Hal is a halogen atom, preferably a chlorine atom or a bromine atom. The reaction may be carried out in a polar aprotic solvent, for example hexamethylphosphortriamide, at a temperature between 0° C. and room temperature. In all the formulae the symbols not described have the same meaning as in formula I.

The invention will be described in greater detail with reference to the ensuing specific examples.

(1) 5-Methoxy-4'-nitrovalerophenone O-(2-aminoethyl)oxime hydrochloride 5.35 Mmol (1.27 g) of 5-methoxy-4'-nitrovalerophenone (melting point 64.5°–65.5° C.), 5.35 mmol (0.80 g) of 2-aminoxyethylamine dihydrochloride and 0.34 ml of pyridine were refluxed for 2 hours in 5 ml of absolute ethanol. After evaporating the reaction mixture to dryness in vacuo, 25 ml of water and 10 ml of 2 N sodium hydroxide solution were added and extracted with 25 and 10 ml, respectively, of methylene chloride. The extracts were dried over sodium sulphate and then evaporated to dryness in vacuo. Toluene was added another two times to the resulting base which was evaporated in vacuo. The residue was dissolved in absolute ethanol and an equimolar quantity of alcoholic hydrochloric acid was added. After the addition of diethyl ether, the title compound crystallized. Melting point 121.5°–122.5° C.

(2) 6-Methoxy-4'-nitrohexaniphenone O-(2-aminoethyl)oxime hydrochloride

135 Mmol (33.7 g) of 6-methoxy-4'-nitrohexanophenone (melting point 50° C.), 135 mmol (20.1 g) of 2-aminoxy-ethylamine dihydrochloride and 100 ml of pyridine were refluxed for 5 hours in 300 ml of absolute ethanol. The reaction mixture was evaporated to dryness in vacuo and the residue, after having been dissolved in 200 ml of water, was washed twice with 100 ml of petroleum ether 40–60. The aqueous solution was rendered alkaline with 200 ml of 2 N sodium hydroxide solution and then extracted four times with 100 ml of ether. The combined ether extracts were washed with 100 ml of water, dried on sodium sulphate and then evaporated to dryness in vacuo. The resulting oil, after the addition of toluene, was evaporated to dryness in vacuo another three times and then dissolved in absolute ethanol. After the addition of an equivalent quantity of alcoholic hydrochloric acid it was evaporated to dryness in vacuo again. The residue was crystallized from alcohol/ether. The resulting crystals were recrystallized twice from acetonitrile and alcohol/ether, respectively. Melting point 92°–93° C.

(3) 3'-Methyl-4'-nitrovalerophenone O-(2-aminoethyl)oxime fumarate (1:1)

5.7 Mmol of 3'-methyl-4'-nitrovalerophenone, 5.7 mmol of 2-aminoxyethylamine dihydrochloride and 0.9 ml of pyridine were refluxed for three hours in 15 ml of absolute ethanol. The base was isolated from the reaction mixture as described in example 2. It was dissolved in an equimolar quantity of ethanolic furmaric acid. Melting point after recrystallization from ethanol 152.5°–154° C.

(4) 3'-Chloro-5-methoxy-4'-nitrovalerophenone O-(2-aminoethyl) oxime fumarate (1:1)

In the same manner as described in example 3, the title compound was obtained from 3'-chloro-5-methoxy-4'-nitrovalerophenone (melting point 54.5°–56° C.) and 2-aminoxyethylamine dihydrochloride. After crystallization from alcohol the melting point was 148°–148.5° C.

(5) 4'-Nitrovalerophenone-O-(2-aminopropyl)oxime hydrochloride

In the same manner as described in Example 2 the title compound was obtained from 4'-nitrovalerophenone (boiling point at 0.03 mm; 128°–132° C.) and 2-aminoxy-1-methylethylamine dihydrochloride. The melting point after recrystallization from acetonitrile/ether was 148°–149° C.

(6) 4'-Nitro-2-propoxyacetophenone O-(2-aminopropyl) oxime fumarate (1:1)

In the same manner as described in Example 3 the title compound was obtained from 4'-nitro-2-propoxyacetophenone (melting point 49°–50° C.) and 2-aminoxy-1-methylethylamine dihydrochloride. The melting point after recrystallization from ethanol was 141°–142° C.

(7) 3'-Chloro-5-methoxy-4'-nitrovalerophenone O-(2aminopropyl) oxime fumarete (1:1)

In the same manner as described in Example 3 the title compound was obtained from 3'-chloro-5-methoxy-4'-nitrovalerophenone (melting point 54.5°–56° C.) and 2-aminoxy-1-methylethylamine dihydrochloride. After crystallization from ethanol/acetonitrile the melting point was 140°–142° C.

(8) 4'-Nitrovalerophenone O-(2-aminoethyl)oxime hydrochloride

10 Mmol of 4'-nitrovalerophenone O-(2-tritylaminoethyl) oxime were dissolved in 50 ml of 90% acetic acid. After standing for three days at room temperature, this reaction mixture was evaporated to dryness in vacuo after which the residue was dissolved in 50 ml of ether. The resulting solution was extracted with 50 ml of 0.2 N hydrochloric acid and the extract, after being rendered alkaline with 10 ml of 2 N sodium hydroxide solution, was extracted with 50 and 25 ml, respectively, of methylene chloride. After drying on sodium sulphate and evaporating in vacuo the resulting base was converted into the title compound with alcoholic hydrochloric acid. After crystallization and recrystallization from ethanol/ether the melting point was 107°–108° C.

(9) 4'-Nitro-2-propoxyacetophenone O-(2-aminoethyl)oxime hydrochloride

10 Mmol of 4'-nitro-2-propoxyacetophenone oxime, 10.4 mmol of 2-chloroethyl amine hydrochloride and 1.4 g of powdered potassium hydroxide were added to 25 ml of dimethyl formamide while stirring at 10° C. After stirring for two days at room temperature the dimethyl formamide was evaporated in vacuo, the residue was brought in water and then 2 N hydrochloric acid was added until pH 3. The remaining oxime was removed by means of ether, after which 30 ml of 2 N sodium hydroxide solution were added. Then three extractions with ether were carried out. The collected ether layers were washed twice with a 5% sodium bicarbonate solution and then dried on sodium sulphate. After removing the ether in vacuo the residue was dissolved in absolute ethanol and converted into the little compound by means of alcoholic hydrochloric acid. After recrystallization from alcohol/ether the melting point was 128°–130° C.

(10) 4'-Nitro-2-propoxyacetophenone O-(2-aminoethyl)oxime hydrochloride (a) 2.3 g of ethylene oxide were led into 30 mmol of 4'-nitro-2-propoxyacetophenone oxime in 50 ml of absolute ethanol in which 0.007 g of lithium had been previously dissolved while stirring and at 45° C. by means of a flow of nitrogen, after which stirring at 60° C. was continued for another hour. After the addition of 0.6 ml of acetic acid it was evaporated to dryness in vacuo. The residue was taken up in ether and washed with water. After drying on sodium sulphate and evaporating the ether a residue was obtained which was purified by means of a silica gel column using methylene chloride as an eluent. After evaporation of the solvent the O-(2-hydroxyethyl) oxime was obtained as an oil.

(b) To a solution of 22 mmol hereof in 120 ml of methylene chloride 4.5 ml of triethylamine were added while stirring at −5° to −10° C., and then 24 mmol (1.9 ml) of mesyl-chloride were added dropwise in 20 minutes. Stirring was continued for another 30 minutes at 0° C. and the reaction mixture was then washed with water, as sodium bicarbonate solution and a saturated sodium chloride solution. After drying on sodium sulphate the methylene chloride was evaporated in vacuo. In this manner the O-(2-mesyloxyethyl) oxime was obtained.

(c) A mixture of 26 mmol thereof in 100 ml of methanol which contained 12 g of ammonia was kept in an autoclave at 80° C. for 16 hours. After cooling, the methanol was removed in vacuo. The residue was stirred with 50 ml of 2 N sodium hydroxide solution and extracted 4 times with ether. The ether layer was washed twice with a 5% sodium bicarbonate solution. After drying on sodium sulphate and distilling off the ether under reduced pressure the resulting oil was converted into the title compound by means of alcoholic hydrochloric acid. After two crystallization from alcohol/ether the melting point was 128°–130° C.

(11) 5-(2;Methoxyethoxy)-4'-nitrovalerophenone O-(2-aminoethyl) oxime fumarate (1:1)

10 Mmol (3.25 g) of 5-(2-methoxyethoxy)-4'-nitrovalerophenone ethylene ketal, 10 mmol (1.49 g) of 2-aminoxyethylamine dihydrochloride and 10 ml of methanol were refluxed for 6 hours. The resulting residue, after evaporating the methanol, was washed three times with ether after having been dissolved in water. The aqueous solution was extracted three times with methylene chloride after previously being rendered alkaline with a sodium hydroxide solution. The combined extracts were washed with a 5% sodium bicarbonate solution and then with water. After drying on sodium sulphate and evaporating the methylene chloride, the free base was obtained, which was converted into the title compound by means of an equimolar quantity of fumeric acid. After crystallization from alcohol the melting point was 134.5°–135.5° C.

(12) 4'-Nitrovalerophenone O-(2-aminoethyl)oxime hydrochloride

4 Mmol (1.23 g) of 4'-aminovalerophenone O-(2-aminoethyl) oxime dihydrochloride (melting point 175°–177° C.) were converted into the free base by means of 2 N sodium hydroxide solution. A solution hereof in 5 ml of methylene chloride was added dropwise while stirring at 25° to 40° C. to 12.3 mmol (2.5 g) of m-chloroperbenzoic acid (85%) in 10 ml of methylene chloride. Stirring at 30° to 35° C. was then continued for another three hours. The precipitate was sucked off and washed with methylene chloride. After the addition of 50 ml of ether to the filtrate and the washing liquid, the mixture was washed three times with 2 N sodium hydroxide solution and finally twice with a 5% sodium bicarbonate solution. After drying on sodium sulphate and removing the ether under reduced pressure, the residue was chromatographed over silical gel with methylene chloride as an eluent. The methylene chloride was distilled off from the eluate, after which the residue was converted into the title compound by means of alcoholic hydrochloride acid. After crystallization from alcohol/ether the melting point was 107°–108° C.

(13) 4'-nitro-2-propylthioacetophenone O-(2-aminoethyl)oxime hydrochloride

6 Mmol (0.54 g) of propylmercaptan were added while stirring to a solution of 6 mmol (0.24 g) of sodium hydroxide in 10 ml of 50% alcohol cooled with ice-water. Stirring was continued for another 10 minutes after which 3 mmol (1.02 g) of 2-bromo-4'-nitroacetophenone O-(2-aminoethyl) oxime hydrochloride (melting point 197° C.) were added within 30 minutes while stirring at a temperature between 0° and 5° C. Stirring was continued for another hour at 5° and then one hour at room temperature. The reaction mixture was evaporated in vacuo and the residue was washed with water and dissolved in methylene chloride. The solution was washed with water and dried over sodium sulphate. After evaporation, a base was obtained which was converted into the title compound by means of alcoholic hydrochloric acid. After recrystallization from acetonitrile/ether the melting point was 122.5°–123.5° C.

(14) 4'-Nitro-2-propoxyacetophenone O-(2-aminoethyl)oxime hydrochloride 0.09 g of 55–60% sodium hydride in mineral oil was added to a solution of 2.0 mmol (0.48 g) of 2-hydroxy-4'-nitroacetophenone O-(2-aminoethyl) oxime (melting point 97°–98° C.) in 5 ml of hexamethyl phosphoric acid triamide while stirring at room temperature. After 4 minutes, 0.20 ml of propyl bromide was added while stirring. The reaction mixture was then stirred at room temperature for another 4 hours, diluted with 50 ml of water and extracted two times with 25 ml of ether. The combined ether extracts were dried on sodium sulphate and evaporated to dryness in vacuo. The residue was chromatographed by means of ethanol/ammonia 95/5 over 15 g of silica gel. The eluate was evaporated to dryness in vacuo and then converted into the title compound by means of alcoholic hydrochloric acid. After crystallization from alcohol-ether the melting point was 125°–130° C.

(15) Tablet 50 mg of 4'-nitro-3'-methylvalerophenone O-(2aminoethyl) oxime HCl
335 mg of lactose
60 mg of potato starch
25 mg of talc
5 mg of magnesium stearate
5 mg of gelatin

(16) Suppository 50 mg of 4'-nitrovalerophenone O-(2-aminopropyl) oxime HCl
1500 mg of suppository mass.

(17) Injection Liquid 25 g of 3'-chloro-4'-nitro-5-methoxyvalerophenone O-(2-aminopropyl) oxime HCl
1.80 g of methyl-p-hydroxybenzoate.
0.20 g of propyl-p-hydroxybenzoate
9.0 g of sodium chloride
4.0 g of poly- (oxyethylene)$_{20}$ sorbitan monoeleate
water to 1000 ml.

What we claim is:

1. Compounds of formula

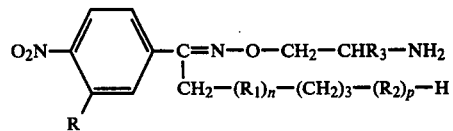

and salts thereof with pharmaceutically acceptable acids, in which formula R is hydrogen, chlorine or methyl, R$_1$ is oxygen or sulphur, R$_2$ is OCH$_2$, CH$_2$OCH$_2$ or OC$_2$H$_4$OCH$_2$, R$_3$ is hydrgen or methyl, n and p have the value 0 or 1 and n+p is 0 or 1.

2. The 4'-Nitrovalerophenone O-(2-aminoethyl)oxime and salts thereof formed with pharmaceutically acceptable acids of claim 1.

3. The 4'-Nitro-2-propylthioacetophenone O-(2-aminoethyl) oxime and salts thereof formed with pharmaceutically acceptable acids of claim 1.

4. The 4'-Nitro-2-propoxyacetophenone O-(2-aminoethyl) oxime and salts thereof formed with pharmaceutically acceptable acids of claim 1.

5. The 5-Methoxy-4'-nitrovalerophenone O-(2-aminoethyl)oxime and salts thereof formed with pharmaceutically acceptable acids of claim 1.

6. The 5-(2-Methoxyethoxy)-4'-nitrovalerophenone O-(2-aminoethyl) oxime and salts thereof formed with pharmaceutically acceptable acids of claim 1.

7. The 6-Methoxy-4'-nitrohexanophenone O-(2-aminoethyl) oxime and salts thereof formed with pharmaceutically acceptable acids of claim 1.

8. The 3'-Methyl-4'-nitrovalerophenone O-(2-aminoethyl) oxime and salts thereof formed with pharmaceutically acceptable acids of claim 1.

9. The 3'-Chloro-5-methoxy-4'-nitrovalerophenone O-(2-aminoethyl)oxime and salts thereof formed with pharmaceutically acceptable acids of claim 1.

10. The 4'-Nitro-valerophenone O-(2-aminopropyl) oxime and salts thereof formed with pharmaceutically acceptable acids of claim 1.

11. The 4'-Nitro-2-propoxyacetophenone O-(2-aminopropyl) oxime and salts thereof formed with pharmaceutically acceptable acids of claim 1.

12. The 3'-Chloro-5-methoxy-4'-nitrovalerophenone O-(2-aminopropyl) oxime and salts thereof formed with pharmaceutically acceptable acids of claim 1.

13. An antidepressive composition comprising a compound of the formula

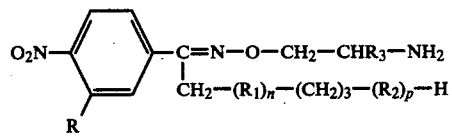

or a salt thereof formed with a pharmaceutically acceptable acid, in which formula R is hydrogen, chlorine or methyl, R$_1$ is oxygen or sulphur, R$_2$ is OCH$_2$CH$_2$OCH$_2$ or OC$_2$H$_4$OCH$_2$ and R$_3$ is hydrogen or methyl and n and p have the value 0 or 1, while the sum of n and p is also 0 or 1 and a pharmaceutically acceptable carrier therefor.

14. A method of treating patients suffering from depression, characterized in that a daily antidepressively effective dose of a compound of the formula

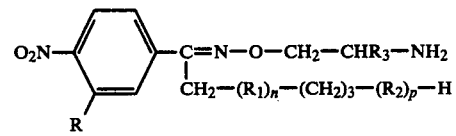

wherein R, R$_1$, R$_2$, R$_3$ and n are defined as in claim 1 or a salt thereof is administered to a patient suffering from depression.

* * * * *

UNITED STATES PATENT AND TRADEMARK OFFICE
CERTIFICATE OF CORRECTION

PATENT NO. : 4,192,893
DATED : March 11, 1980
INVENTOR(S) : Hendricus B. A. Welle et al.

It is certified that error appears in the above—identified patent and that said Letters Patent is hereby corrected as shown below:

On the Title Page

Assignee should read -- Duphar International Research B.V., the Netherland --.

Signed and Sealed this

Thirtieth Day of September 1980

[SEAL]

*Attest:*

SIDNEY A. DIAMOND

*Attesting Officer*     *Commissioner of Patents and Trademark*